United States Patent
Recio, III et al.

(10) Patent No.: US 9,676,706 B2
(45) Date of Patent: Jun. 13, 2017

(54) LOW PH METAL-FREE PREPARATION OF AMINATED ORGANIC ACID

(71) Applicant: Halliburton Energy Services, Inc., Houston, TX (US)

(72) Inventors: Antonio Recio, III, Humble, TX (US); Enrique Antonio Reyes, Tomball, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/779,703

(22) PCT Filed: Oct. 17, 2014

(86) PCT No.: PCT/US2014/061129
§ 371 (c)(1),
(2) Date: Sep. 24, 2015

(87) PCT Pub. No.: WO2016/060685
PCT Pub. Date: Apr. 21, 2016

(65) Prior Publication Data
US 2016/0229797 A1     Aug. 11, 2016

(51) Int. Cl.
*E21B 43/04*     (2006.01)
*E21B 43/22*     (2006.01)
(Continued)

(52) U.S. Cl.
CPC ............ *C07C 303/04* (2013.01); *C09K 8/035* (2013.01); *C09K 8/50* (2013.01); *C09K 8/52* (2013.01);
(Continued)

(58) Field of Classification Search
CPC ......... C09K 8/68; E21B 43/26; E21B 43/267; E21B 33/13; E21B 33/138; E21B 43/04; E21B 43/02
See application file for complete search history.

(56) References Cited

U.S. PATENT DOCUMENTS

| 7,638,469 B2 | 12/2009 | Heidenfelder et al. |
| 7,776,798 B2 | 8/2010 | Subramanian et al. |

(Continued)

FOREIGN PATENT DOCUMENTS

| AU | 2011343383 | 6/2013 |
| AU | 2011343382 | 7/2015 |

(Continued)

OTHER PUBLICATIONS

"International Application Serial No. PCT/US2014/061129, International Search Report mailed Jun. 29, 2015", 3 pgs.
(Continued)

*Primary Examiner* — Zakiya W Bates
(74) *Attorney, Agent, or Firm* — Chamberlain Hrdlicka

(57) ABSTRACT

The invention provides a process for making compounds according to Formula I:

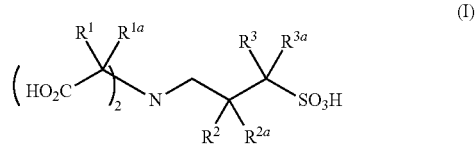

where $R^1$, $R^{1a}$, $R^2$, $R^{2a}$, $R^3$ and $R^{3a}$ are defined as set forth in the specification. Formula I compounds are useful as chelants and stabilizers of cations in aqueous media and the (Continued)

invention therefore provides a method for using the compounds in the treatment of subterranean formations, such as in acidizing operations.

22 Claims, 3 Drawing Sheets

(51) Int. Cl.

| | |
|---|---|
| E21B 43/26 | (2006.01) |
| C07C 303/04 | (2006.01) |
| C09K 8/86 | (2006.01) |
| C09K 8/035 | (2006.01) |
| C09K 8/74 | (2006.01) |
| C09K 8/84 | (2006.01) |
| C09K 8/50 | (2006.01) |
| C09K 8/52 | (2006.01) |
| C09K 8/62 | (2006.01) |
| E21B 21/06 | (2006.01) |
| E21B 43/16 | (2006.01) |

(52) U.S. Cl.
CPC ............... *C09K 8/62* (2013.01); *C09K 8/74* (2013.01); *C09K 8/84* (2013.01); *C09K 8/86* (2013.01); *E21B 21/062* (2013.01); *E21B 43/04* (2013.01); *E21B 43/16* (2013.01); *E21B 43/26* (2013.01); *C09K 2208/02* (2013.01)

(56) References Cited

U.S. PATENT DOCUMENTS

| | | |
|---|---|---|
| 8,316,941 B2 | 11/2012 | Frenier et al. |
| 2006/0102349 A1 | 5/2006 | Brady et al. |
| 2007/0187648 A1 | 8/2007 | Welton et al. |
| 2010/0276152 A1 | 11/2010 | de Wolf et al. |
| 2011/0257431 A1 | 10/2011 | Baumann et al. |
| 2012/0202720 A1 | 8/2012 | de Wolf et al. |
| 2012/0264973 A1 | 10/2012 | Baumann et al. |
| 2012/0302783 A1 | 11/2012 | Baumann et al. |
| 2013/0264060 A1 | 10/2013 | de Wolf et al. |
| 2013/0267446 A1 | 10/2013 | de Wolf et al. |
| 2013/0274154 A1 | 10/2013 | Nasr-El-Din et al. |
| 2014/0296113 A1 | 10/2014 | Reyes et al. |

FOREIGN PATENT DOCUMENTS

| | | |
|---|---|---|
| AU | 2011343384 | 7/2015 |
| AU | 2011343272 | 8/2015 |
| AU | 2011200525 | 4/2016 |
| CA | 2321543 | 2/2009 |
| CA | 2483839 | 1/2011 |
| CA | 2820910 | 6/2012 |
| CA | 2820918 | 6/2012 |
| CA | 2820920 | 6/2012 |
| CA | 2820944 | 6/2012 |
| CA | 2835511 | 11/2012 |
| CA | 2838297 | 12/2012 |
| CA | 2838299 | 12/2012 |
| CA | 2711634 | 9/2016 |
| EP | 2229423 | 9/2010 |
| JP | 10158226 | 6/1998 |
| JP | 2002356464 | 12/2002 |
| WO | 9946234 | 9/1999 |
| WO | 2009024518 | 2/2009 |
| WO | 2009024519 | 2/2009 |
| WO | 2009086954 | 7/2009 |
| WO | 2009127982 | 10/2009 |
| WO | 2011151517 | 12/2011 |
| WO | 2012080296 | 6/2012 |
| WO | 2012080297 | 6/2012 |
| WO | 2012080298 | 6/2012 |
| WO | 2012080463 | 6/2012 |
| WO | 2012160008 | 11/2012 |
| WO | 2012171857 | 12/2012 |
| WO | 2012171858 | 12/2012 |
| WO | 2012171859 | 12/2012 |
| WO | 2013092440 | 6/2013 |
| WO | 2013092780 | 6/2013 |
| WO | 2013120806 | 8/2013 |

OTHER PUBLICATIONS

"International Application Serial No. PCT/US2014/061129, Written Opinion mailed Jun. 29, 2015", 4 pgs.

"National Center for Biotechnology Information. PubChem Compound Database: CID=125932", [Online]. Retrieved from the Internet: <http://pubchem.ncbi.nlm.nih.gov/compound/125932>, (Aug. 8, 2005), 9 pgs.

Lenz, G. R., et al., "Metal Chelates of Some Sulfur-containing Amino Acids", Biochemistry, vol. 3, No. 6, (Jun. 11, 1964), 745-750.

De Wolf et al., SPE 168145: "Evaluation of Environmentally Friendly Chelating Agents for Applications in the Oil and Gas Industry," SPE International, SPE International Symposium and Exhibition on Formation Damage Control, 2014: 1-15.

Frenier et al., SPE 71696: "Hydroxyaminocarboxylic Acids Produce Superior Formulations for Matrix Stimulation of Carbonates at High Temperatures," SPE International, 2001 SPE Annual Technical Conference and Exhibition, 2001: pp. 1-16.

Gdanski, SPE 27404: "Fluosilicate Solubilities Affect HF Acid Compositions," SPE Production & Facilities, Nov. 1994: pp. 225-229.

Kolodydynska, "Chelating Agents of a New Generation as an Alternative to Conventional Chelators for Heavy Metal Ions Removal from Different Waste Waters," Expanding Issues in Desalination, Chapter 17, InTech, ed. Ning, Sep. 2011: pp. 339-370, <http://www.intechopen.com/books/expanding-issues-in-desalination/chelating-agents-of-a-new-generation-as-an-alternative-to-conventional-chelators-for-heavy-metal-ion>.

Li et al., SPE 128091: "Impact of Organic Acids/Chelating Agents on the Rheological Properties of an Amidoamine Oxide Surfactant," SPE International, 2010 SPE International Symposium and Exhibition on Formation Damage Control, 2010: pp. 1-33.

Parkinson et al., SPE 128043: "Stimulation of Multilayered High-Carbonate-Content Sandstone Formations in West Africa Using Chelant-Based Fluids and Mechanical Diversion," SPE International, 2010 SPE International Symposium and Exhibition on Formation Damage Control, 2010: pp. 1-10.

Reyes et al., SPE 164380: "Carbonate Stimulation with Biodegradable Chelating Agent Having Broad Unique Spectrum (pH, Temperature, Concentration) Activity," SPE International, SPE Middle East Oil and Gas Show and Conference, 2013: pp. 1-11.

Reyes et al., SPE 165142: "Properties and Applications of an Alternative Aminopolycarboxylic Acid for Acidizing of Sandstones and Carbonates," SPE International, SPE European Formation Damage Conference and Exhibition, 2013: pp. 1-18.

US 9,676,706 B2

LOW PH METAL-FREE PREPARATION OF AMINATED ORGANIC ACID

PRIORITY APPLICATION

This application is a U.S. National Stage Filing under 35 U.S.C. 371 from International Application No. PCT/US2014/061129, filed Oct. 17, 2014; which application is incorporated herein by reference in its entirety.

BACKGROUND OF THE INVENTION

The use of chelating or sequestering agents in acidizing technology allows for the design of fluid systems offering benefits over conventional acidizing treatments (see H. Nasr. El-Din et. al., 2014 SPE 168145; Reyes et. al., 2013 SPE 165142; Reyes et. al., 2013 SPE 164380; H. Nasr. El-Din et. al., 2011 SPE 128091; M. Parkinson, et. al., 2010 SPE 128043; and W. W. Frenier et. al., 2001 SPE 71696). Specifically, the agents give rise to improved complexation of cations and stabilize the minerals formed within a formation matrix as a result of an acidizing treatment. For example, when chelating agents along with HF acid are utilized in sandstone matrix acidizing treatments, cations formed by the dissolution of minerals such as silica, feldspar, and feldspar are held in solution via cation-chelation, reducing precipitation of salts formed from the cations, resulting in improved matrix permeability (U.S. Pat. No. 8,316,941). For this reason, the solubility profile (e.g., pH for dissolution) of the chelant as well as the nature of the chelant that is introduced into the treatment fluid (e.g., as the acid, sodium, or potassium salt) is important.

Aminopolycarboxylate chelants akin to ethylenediaminetetracetic acid (EDTA) are one class of compounds useful in the oil and gas industry as anti-scalants, iron-sequestrants, and standalone matrix stimulation fluids. These organic compounds function as reactivity modifiers of multivalent cations. For instance, chelating reagents such as N-(2-hydroxyethyl)ethylenediaminetriacetic acid (HEDTA), glutamic acid N, N-diacetic acid (GLDA), methyl-glycinediacetic acid (MGDA), and hydroxyiminodisuccinic acid (HIDS) chelate or complex the cations formed during the dissolution of formation minerals resulting in improved solubility profiles (Dorota Kolodynska (2011). "Chelating Agents of a New Generation as an Alternative to Conventional Chelators for Heavy Metal Ions Removal from Different Waste Waters (Chapter 17)" Expanding Issues in Desalination, Prof. Robert Y. Ning (Ed.)).

Some challenges attach to the use of the foregoing chelating agents. First, commercially available chelants are typically supplied as their sodium or potassium salts. In order to remove the sodium or potassium ions and generate a neutral chelating agent, the pH must be lowered by introduction of hydrochloric acid for effective carbonate acidizing. This also has added consequences when having to employ hydrofluoric acid (HF) in sandstone acidizing. Post-synthesis modification, such as ion exchange process, of the sodium salt of a chelant, for instance, can be implemented to produce the ammonium salt of the chelant which is then free of cation ($Na^+$ or $K^+$) or in low concentration (see US20130281329).

Second, the post-synthesis acidification mentioned above liberates large amounts of unwanted cations into oil well treatment fluids. Specifically, sodium ($Na^+$) and potassium ($K^+$) cations strongly associate with fluoride and fluorosilicates, causing the rapid precipitation of metallated-fluorides or metallated-silicates, and thereby mitigating the efficacy of the acidizing treatment (see R. D. Gdanski, 1994 SPE 27404).

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

Figure 1:
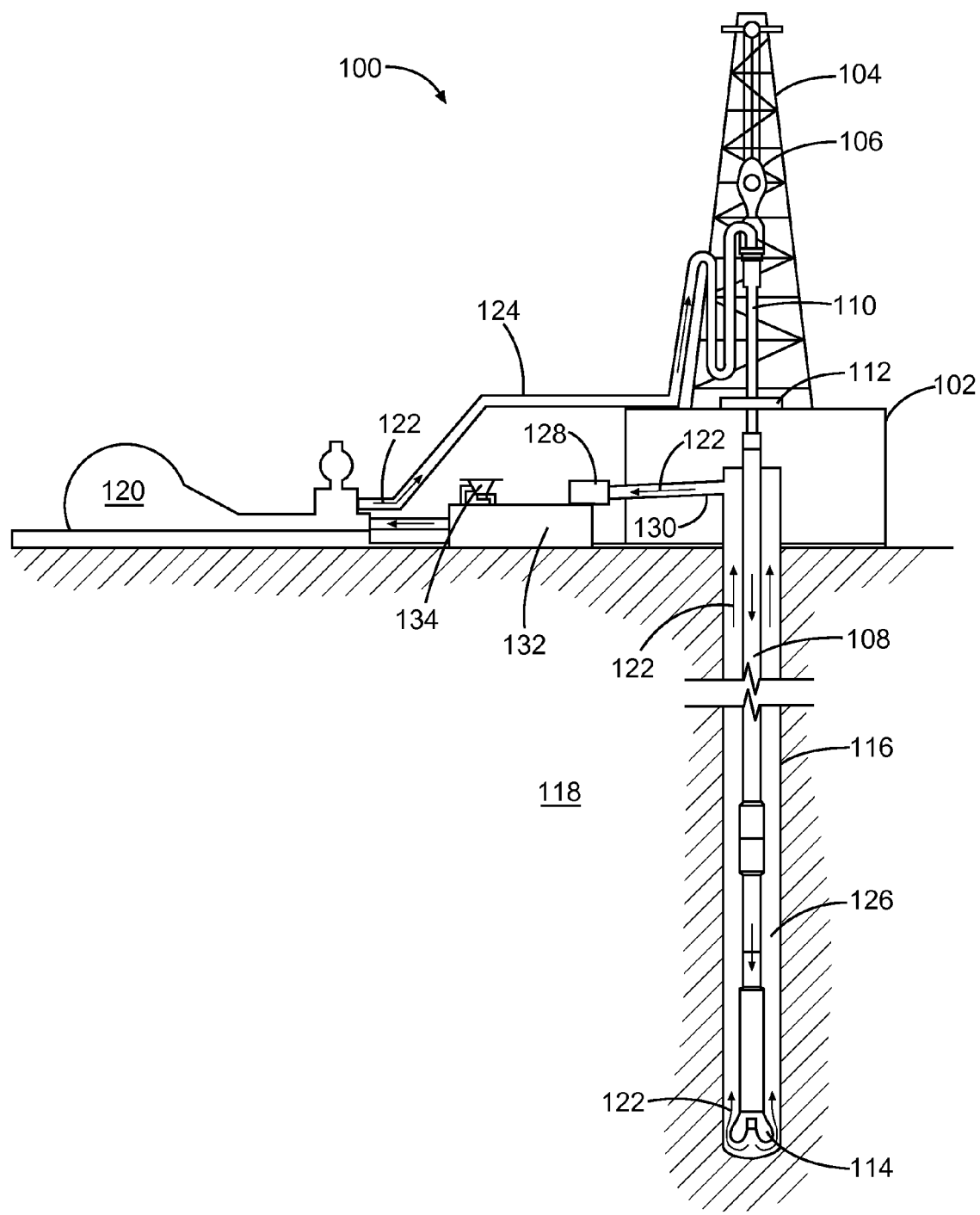
FIG. 1 illustrates a drilling assembly in accordance with various embodiments.

In satisfying the needs described above, the present invention provides a convenient and one-pot process for synthesizing Formula I compounds, as described herein, that are free of metal cations. The compounds may be synthesized at very low pH and are therefore immediately useful in treating subterranean formations, such as in acidizing operations as described herein. The invention also provides a Formula I composition and its method of use in treating a subterranean formation, such as in fracking operations in hydrocarbon wells.

Reference will now be made in detail to certain embodiments of the disclosed subject matter, examples of which are illustrated in part by the accompanying drawings. While the disclosed subject matter will be described in conjunction with the enumerated claims, the exemplified subject matter is not intended to limit the claims to the disclosed subject matter.

DEFINITIONS

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "downhole" as used herein refers to under the surface of the earth, such as a location within or fluidly connected to a wellbore.

As used herein, the term "fluid" refers to liquids and gels, unless otherwise indicated.

As used herein, the term "subterranean material" or "subterranean formation" refers to any material under the surface of the earth, including under the surface of the bottom of the ocean. For example, a subterranean material can be any section of a wellbore and any section of an underground formation in fluid contact with the wellbore, including any materials placed into the wellbore such as cement, drill shafts, liners, tubing, or screens. In some examples, a subterranean material is any below-ground area that can produce liquid or gaseous petroleum materials, water, or any section below-ground in fluid contact therewith.

Some embodiments of the invention also relate to methods of using the composition in subterranean formations penetrated by wellbores.

As used herein, the term "drilling fluid" refers to fluids, or slurries used in drilling operations downhole, such as the formation of a wellbore.

As used herein, the term "stimulation fluid" refers to fluids or slurries used downhole during stimulation activities of the well that can increase the production of a well, including perforation activities. In some examples, a stimulation fluid can include a fracturing fluid or an acidizing fluid.

As used herein, the term "clean-up fluid" refers to fluids or slurries used downhole during clean-up activities of the well, such as any treatment to remove material obstructing the flow of desired material from the subterranean formation. In one example, a clean-up fluid can be an acidification treatment to remove material formed by one or more perforation treatments. In another example, a clean-up fluid can be used to remove a filter cake.

As used herein, the term "fracturing fluid" refers to fluids or slurries used downhole during fracturing operations.

As used herein, the term "spotting fluid" refers to fluids or slurries used downhole during spotting operations and can be any fluid designed for localized treatment of a downhole region. In one example, a spotting fluid can include a lost circulation material for treatment of a specific section of a wellbore, such as to seal off fractures in a wellbore and prevent sag. In another example, a spotting fluid can include a water control material. In some examples, a spotting fluid can be designed to free a stuck piece of drilling or extraction equipment; can reduce torque and drag with drilling lubricants; prevent differential sticking; promote wellbore stability; and can help to control mud weight.

As used herein, the term "production fluid" refers to fluids or slurries used downhole during the production phase of a well. Production fluids can include downhole treatments designed to maintain or increase the production rate of a well, such as perforation treatments, clean-up treatments or remedial treatments.

As used herein, the term "completion fluid" refers to fluids or slurries used downhole during the completion phase of a well.

As used herein, the term "remedial treatment fluid" refers to fluids or slurries used downhole for remedial treatment of a well. Remedial treatments can include treatments designed to increase or maintain the production rate of a well, such as stimulation or clean-up treatments.

As used herein, the term "abandonment fluid" refers to fluids or slurries used downhole during or preceding the abandonment phase of a well.

As used herein, the term "acidizing fluid" or "acidic treatment fluids" refers to fluids or slurries used downhole during acidizing treatments downhole. Acidic treatment fluids can be used during or in preparation for any subterranean operation wherein a fluid may be used. Suitable subterranean operations may include, but are not limited to, acidizing treatments (e.g., matrix acidizing or fracture acidizing), wellbore clean-out treatments, and other operations where a treatment fluid of the present invention may be useful. In a matrix acidizing procedure, for example, an aqueous acidic treatment fluid (e.g., a treatment comprising the emulsion described herein, an aqueous base fluid, and spent acid) is introduced into a subterranean formation via a wellbore therein under pressure so that the acidic treatment fluid flows into the pore spaces of the formation and reacts with (e.g., dissolves) acid-soluble materials therein. As a result, the pore spaces of that portion of the formation are enlarged, and the permeability of the formation may increase. The flow of hydrocarbons from the formation therefore may be increased because of the increase in formation conductivity caused, among other factors, by dissolution of the formation material.

In fracture acidizing procedures, one or more fractures are produced in the formation(s) and an acidic treatment fluid is introduced into the fracture(s) to etch flow channels therein. Acidic treatment fluids also may be used to clean out wellbores to facilitate the flow of desirable hydrocarbons. Other acidic treatment fluids may be used in diversion processes and wellbore clean-out processes. For example, acidic treatment fluids can be useful in diverting the flow of fluids present within a subterranean formation (e.g., formation fluids and other treatment fluids) to other portions of a formation, for example, by invading higher permeability portions of a formation with a fluid that has high viscosity at low shear rates.

As used herein, the term "cementing fluid" refers to fluids or slurries used during cementing operations of a well. For example, a cementing fluid can include an aqueous mixture including at least one of cement and cement kiln dust. In another example, a cementing fluid can include a curable resinous material, such as a polymer, that is in an at least partially uncured state.

As used herein, the term "fluid control material" (e.g., a "water control material") refers to a solid or liquid material that, by virtue of its viscosification in the flowpaths producing a fluid (e.g., water) alters, reduces or blocks the flow rates of such fluids into the wellbore, such that hydrophobic material can more easily travel to the surface and such that hydrophilic material (including water) can less easily travel to the surface. For example, a fluid control material can be used to treat a well to cause a proportion of a fluid produced, which may include water, to decrease and to cause the proportion of hydrocarbons produced to increase, such as by selectively causing the material to form a viscous plug between water-producing subterranean formations and the wellbore, while still allowing hydrocarbon-producing formations to maintain output.

In some embodiments, the fluid control material mitigates (e.g., reduces, stops or diverts) the flow of fluids (e.g., treatment fluids and water) through a portion of a subterranean formation that is penetrated by the well such that the flow of the fluid into high-permeability portions of the formation is mitigated. For example, in an injection well, it may be desirable to seal off high-permeability portions of a subterranean formation that would otherwise accept most of an injected treatment fluid. By sealing off the high-permeability portions of the subterranean formation, the injected treatment fluid may thus penetrate less permeable portions of the subterranean formation. In other embodiments, the fluid control material helps mitigate the production of undesired fluids (e.g., water) from a well by at least sealing off one or more permeable portions of a treated subterranean formation.

As used herein, the term "packing fluid" refers to fluids or slurries that can be placed in the annular region of a well, between tubing and outer casing above a packer. In various examples, the packer fluid can provide hydrostatic pressure in order to lower differential pressure across a sealing element; lower differential pressure on the wellbore and casing to prevent collapse; and protect metals and elastomers from corrosion.

"Alkyl" refers to straight, branched chain, or cyclic hydrocarbyl groups including from 1 to about 20 carbon atoms. For instance, an alkyl can have from 1 to 10 carbon atoms or 1 to 5 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$'—CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups.

The phrase "substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The terms "alkylene" and "substituted alkylene" refer to divalent alkyl and divalent substituted alkyl, respectively. Examples of alkylene include without limitation, ethylene (—CH$_2$—CH$_2$—).

"Alkene" refers to straight, branched chain, or cyclic hydrocarbyl groups including from 2 to about 20 carbon atoms having one or more carbon to carbon double bonds, such as 1 to 3, 1 to 2, or at least one carbon to carbon double bond. "Substituted alkene" refers to alkene substituted at 1 or more, e.g., 1, 2, 3, 4, 5, or even 6 positions, which substituents are attached at any available atom to produce a stable compound, with substitution as described herein. "Optionally substituted alkene" refers to alkene or substituted alkene.

The term "alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or "alkynyl" refers to a straight or branched chain unsaturated hydrocarbon having the indicated number of carbon atoms and at least one triple bond. Examples of a (C$_2$-C$_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a (C$_1$-C$_6$)alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O— neopentyl (neopentoxy), —O-hexyl (hexyloxy), —O-isohexyl (isohexyloxy), and —O-neohexyl (neohexyloxy).

The term "aryl," alone or in combination refers to an aromatic monocyclic or bicyclic ring system such as phenyl or naphthyl. "Aryl" also includes aromatic ring systems that are optionally fused with a cycloalkyl ring as herein defined.

A "substituted aryl" is an aryl that is independently substituted with one or more substituents attached at any available atom to produce a stable compound, wherein the substituents are as described herein. "Optionally substituted aryl" refers to aryl or substituted aryl.

"Arylene" denotes divalent aryl, and "substituted arylene" refers to divalent substituted aryl. "Optionally substituted arylene" refers to arylene or substituted arylene.

The term "heteroatom" refers to N, O, and S. Inventive compounds that contain N or S atoms can be optionally oxidized to the corresponding N-oxide, sulfoxide or sulfone compounds.

"Heteroaryl," alone or in combination with any other moiety described herein, refers to a monocyclic aromatic ring structure containing 5 or 6 ring atoms, or a bicyclic aromatic group having 8 to 10 atoms, containing one or more, such as 1 to 4, 1 to 3, or 1 to 2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Heteroaryl" also contemplates fused ring systems wherein the heteroaryl is fused to an aryl or cycloalkyl ring as defined herein.

A "substituted heteroaryl" is a heteroaryl that is independently substituted, unless indicated otherwise, with one or more, e.g., 1, 2, 3, 4 or 5, attached at any available atom to produce a stable compound, wherein the substituents are as described herein. "Optionally substituted heteroaryl" refers to heteroaryl or substituted heteroaryl.

"Heteroarylene" refers to divalent heteroaryl, and "substituted heteroarylene" refers to divalent substituted heteroaryl. "Optionally substituted heteroarylene" refers to heteroarylene or substituted heteroarylene.

"Heterocycloalkyl" means a saturated or unsaturated non-aromatic monocyclic, bicyclic, tricyclic or polycyclic ring system that has from 5 to 14 atoms in which from 1 to 3 carbon atoms in the ring are replaced by heteroatoms of O, S or N. A heterocycloalkyl is optionally fused with benzo or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl.

"Optionally substituted heterocycloalkyl" denotes heterocycloalkyl that is substituted with 1 to 3 substituents, e.g., 1, 2 or 3 substituents, attached at any available atom to produce a stable compound, wherein the substituents are as described herein.

"Heteroalkyl" means a saturated alkyl group having from 1 to about 20 carbon atoms, 1 to 10 carbon atoms, 1 to 6 carbon atoms, or 1 to 3 carbon atoms, in which from 1 to 3 carbon atoms are replaced by heteroatoms of O, S or N. Heteroalkyl is also intended to include oxidized S or N, such as sulfinyl, sulfonyl and N-oxide of a tertiary ring nitrogen. The point of attachment of the heteroalkyl substituent is at an atom such that a stable compound is formed. Examples of heteroalkyl groups include, but are not limited to, N-alkylaminoalkyl (e.g., $CH_3NHCH_2$—), N,N-dialkylaminoalkyl (e.g., $(CH_3)_2NCH_2$—), and the like.

"Heteroalkylene" refers to divalent heteroalkyl. The term "optionally substituted heteroalkylene" refers to heteroalkylene that is substituted with 1 to 3 substituents, e.g., 1, 2 or 3 substituents, attached at any available atom to produce a stable compound, wherein the substituents are as described herein.

"Heteroalkene" means a unsaturated alkyl group having from 1 to about 20 carbon atoms, 1 to 10 carbon atoms, 1 to 6 carbon atoms, or 1 to 3 carbon atoms, in which from 1 to 3 carbon atoms are replaced by heteroatoms of O, S or N, and having 1 to 3, 1 to 2, or at least one carbon to carbon double bond or carbon to heteroatom double bond.

"Heteroalkenylene" refers to divalent heteroalkene. The term "optionally substituted heteroalkenylene" refers to heteroalkenylene that is substituted with 1 to 3 substituents, e.g., 1, 2 or 3 substituents, attached at any available atom to produce a stable compound, wherein the substituents are as described herein.

The term "cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring as defined above. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below.

The term "cycloalkenyl" refers to a monocyclic, bicyclic, tricyclic, or polycyclic, 3- to 14-membered ring system, which is unsaturated. The cycloalkenyl group may be attached via any atom. Representative examples of cycloalkenyl include, but are not limited to, cyclopropenyl, cyclobutenyl, cyclopentenyl and cyclohexenyl.

The term "cycloalkylene" refers to divalent cycloalkyl. The term "optionally substituted cycloalkylene" refers to cycloalkylene that is substituted with 1 to 3 substituents, e.g., 1, 2 or 3 substituents, attached at any available atom to produce a stable compound, wherein the substituents are as described herein.

The term "nitrile or cyano" can be used interchangeably ands refer to a —CN group.

The term "oxo" refers to a =O atom attached to a saturated or unsaturated ($C_3$-$C_8$) cyclic or a ($C_1$-$C_8$) acyclic moiety. The =O atom can be attached to a carbon, sulfur, and nitrogen atom that is part of the cyclic or acyclic moiety.

The term "amine or amino" refers to an —$NR^dR^e$ group wherein $R^d$ and $R^e$ each independently refer to a hydrogen, ($C_1$-$C_8$)alkyl, aryl, heteroaryl, heterocycloalkyl, ($C_1$-$C_8$)haloalkyl, and ($C_1$-$C_6$)hydroxyalkyl group.

The term "amide" refers to a —NR'R"C(O)— group wherein R' and R" each independently refer to a hydrogen, ($C_1$-$C_8$)alkyl, or ($C_3$-$C_6$)aryl.

The term "carboxamido" refers to a —C(O)NR'R" group wherein R' and R" each independently refer to a hydrogen, ($C_1$-$C_8$)alkyl, or ($C_3$-$C_6$)aryl.

The term "aryloxy" refers to an —O-aryl group having the indicated number of carbon atoms. Examples of aryloxy groups include, but are not limited to, phenoxy, napthoxy and cyclopropeneoxy.

The term "haloalkoxy," refers to an —O—($C_1$-$C_6$)alkyl group wherein one or more hydrogen atoms in the $C_1$-$C_8$ alkyl group is replaced with a halogen atom, which can be the same or different. Examples of haloalkyl groups include, but are not limited to, difluoromethoxy, trifluoromethoxy, 2,2,2-trifluoroethoxy, 4-chlorobutoxy, 3-bromopropyloxy, pentachloroethoxy, and 1,1,1-trifluoro-2-bromo-2-chloroethoxy.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —$CH_2OOH$, —$CH_2CH_2OH$, —$CH_2CH_2CH_2OOH$, —$CH_2CH_2CH_2CH_2OOH$, —$CH_2CH_2CH_2CH_2CH_2OH$, —$CH_2CH_2CH_2CH_2CH_2CH_2OH$, and branched versions thereof.

The term "alkylsulfonyl" refers to a $(C_1-C_6)$alkyl group wherein one or more hydrogen atoms in the $C_1-C_6$ alkyl group is replaced with a —S(O)$_a$ group. Subscript "a" can either be 1 or 2, so as to give an alkyl sulfoxide (sulfinyl group), or an alkyl sulfone respectively. Examples of alkylsulfonyl groups include, but are not limited to dimethylsulfoxide, ethylmethyl sulfoxide, and methylvinylsulfone.

The term "haloalkyl," refers to an $(C_1-C_6)$alkyl group wherein one or more hydrogen atoms in the $C_1-C_6$ alkyl group is replaced with a halogen atom, which can be the same or different. Examples of haloalkyl groups include, but are not limited to, difluoromethyl, trifluoromethyl, 2,2,2-trifluoroethyl, 4-chlorobutyl, 3-bromopropylyl, pentachloroethyl, and 1,1,1-trifluoro-2-bromo-2-chloroethyl.

The term "aminoalkyl," refers to an $(C_1-C_6)$alkyl group wherein one or more hydrogen atoms in the $C_1-C_6$ alkyl group is replaced with a —NR$^d$R$^e$ group, where R$^d$ and R$^e$ can be the same or different, for example, R$^d$ and R$^e$ each independently refer to a hydrogen, $(C_1-C_8)$alkyl, aryl, heteroaryl, heterocycloalkyl, $(C_1-C_8)$haloalkyl, and $(C_1-C_6)$ hydroxyalkyl group. Examples of aminoalkyl groups include, but are not limited to, aminomethyl, aminoethyl, 4-aminobutyl and 3-aminobutylyl.

The term "thioalkyl" or "alkylthio" refers to a $(C_1-C_6)$ alkyl group wherein one or more hydrogen atoms in the $C_1-C_6$ alkyl group is replaced with a —SR group, wherein $R^1$ is selected from the group consisting of hydrogen, $(C_1-C_6)$alkyl and $(C_3-C_{14})$aryl.

"Amino $(C_1-C_6)$alkylene" refers to a divalent alkylene wherein one or more hydrogen atoms in the $C_1-C_6$ alkylene group is replaced with a —NR$^d$R$^e$ group. Examples of amino $(C_1-C_6)$alkylene include, but are not limited to, aminomethylene, aminoethylene, 4-aminobutylene and 3-aminobutylylene.

The term "sulfonamide" refers to an —NR$^g$S(O)$_2$R$^h$ group where R$^g$ and R$^h$ each independently refer to a hydrogen, $(C_1-C_8)$alkyl, aryl, heteroaryl, heterocycloalkyl, $(C_1-C_8)$haloalkyl, and a $(C_1-C_6)$hydroxyalkyl group.

A "hydroxyl" or "hydroxy" refers to an —OH group.

The term "$(C_3-C_{14})$aryl-$(C_1-C_6)$alkylene" refers to a divalent alkylene wherein one or more hydrogen atoms in the $C_1-C_6$ alkylene group is replaced by a $(C_3-C_{14})$aryl group. Examples of $(C_3-C_{14})$aryl-$(C_1-C_6)$alkylene groups include without limitation 1-phenylbutylene, phenyl-2-butylene, 1-phenyl-2-methylpropylene, phenylmethylene, phenylpropylene, and naphthylethylene.

The term "$(C_3-C_{14})$heteroaryl-$(C_1-C_6)$alkylene" refers to a divalent alkylene wherein one or more hydrogen atoms in the $C_1-C_6$ alkylene group is replaced by a $(C_3-C_{14})$heteroaryl group. Examples of $(C_3-C_{14})$heteroaryl-$(C_1-C_6)$alkylene groups include without limitation 1-pyridylbutylene, quinolinyl-2-butylene and 1-pyridyl-2-methylpropylene.

The term "$(C_3-C_{14})$heterocycloalkyl-$(C_1-C_6)$alkylene" refers to a divalent alkylene wherein one or more hydrogen atoms in the $C_1-C_6$ alkylene group is replaced by a $(C_3-C_{14})$ heterocycloalkyl group. Examples of $(C_3-C_{14})$heterocycloalkyl-$(C_1-C_6)$alkylene groups include without limitation 1-morpholinopropylene, azetidinyl-2-butylene and 1-tetrahydrofuranyl-2-methylpropylene.

The term "$(C_3-C_{14})$heteroaryl-$(C_1-C_{14})$hetercycloalkylene" refers to a divalent heterocycloalkylene wherein one or more hydrogen atoms in the $C_1-C_6$ heterocycloalkylene group is replaced by a $(C_3-C_{14})$heteroaryl group. Examples of $(C_3-C_{14})$heteroaryl-$(C_1-C_6)$heterocycloalkylene groups include without limitation pyridylazetidinylene and 4-quinolino-1-piperazinylene.

The term "$(C_3-C_{14})$aryl-$(C_1-C_{14})$heterocycloalkylene" refers to a divalent heterocycloalkylene wherein one or more hydrogen atoms in the $C_1-C_{14}$ heterocycloalkylene group is replaced by a $(C_3-C_{14})$aryl group. Examples of $(C_3-C_{14})$ aryl-$(C_1-C_{14})$heterocycloalkylene groups include without limitation 1-naphthyl-piperazinylene, phenylazetidinylene, and phenylpiperidinylene.

The term "$(C_3-C_{14})$aryl-$(C_1-C_6)$alkyl-$(C_1-C_{14})$heterocycloalkylene" refers to a divalent heterocycloalkylene wherein one or more hydrogen atoms in the $C_1-C_{14}$ heterocycloalkylene group is replaced by a $(C_1-C_6)$-alkyl group that is further substituted by replacing one or more hydrogen atoms of the $(C_1-C_6)$ alkyl group with a $(C_3-C_{14})$aryl group.

The term "$(C_3-C_{14})$heteroaryl-$(C_1-C_6)$alkyl-$(C_1-C_{14})$heterocycloalkylene" refers to a divalent heterocycloalkylene wherein one or more hydrogen atoms in the $C_1-C_{14}$ heterocycloalkylene group is replaced by a $(C_1-C_6)$ alkyl group that is further substituted by replacing one or more hydrogen atoms of the $(C_1-C_6)$ alkyl group with a $(C_3-C_{14})$heteroaryl group.

The term "$(C_3-C_{14})$heterocycloalkyl-$(C_1-C_6)$alkyl-$(C_1-C_{14})$heterocycloalkylene" refers to a divalent heterocycloalkylene wherein one or more hydrogen atoms in the $C_1-C_{14}$ heterocycloalkylene group is replaced by a $(C_1-C_6)$ alkyl group that is further substituted by replacing one or more hydrogen atoms of the $(C_1-C_6)$ alkyl group with a $(C_3-C_{14})$heterocycloalkyl group.

The term "$(C_3-C_{14})$aryl-$(C_1-C_{14})$cycloalkylene" refers to a divalent cycloalkylene that is monocyclic, bicyclic or polycyclic and wherein one or more hydrogen atoms in the $(C_1-C_{14})$cycloalkylene group is replaced by a $(C_3-C_{14})$aryl group. Examples of $(C_3-C_{14})$aryl-$(C_1-C_{14})$cycloalkylene groups include without limitation phenylcyclobutylene, phenyl-cyclopropylene and 3-phenyl-2-methylbutylene-1-one.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

Process of Synthesizing

In one embodiment, the invention provides a process for synthesizing a compound according to Formula I:

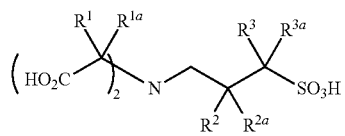

(I)

comprising contacting a compound of Formula A:

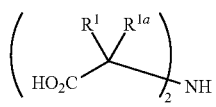

(A)

with a compound of Formula B:

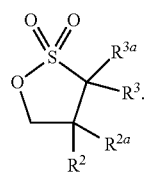

(B)

In Formulae I, A, and B, substituents $R^1$, $R^{1a}$, $R^2$, $R^{2a}$, $R^3$ and $R^{3a}$ are independently selected from the group consisting of H, —OH, halo, straight or branched $(C_1-C_6)$alkyl, straight or branched $(C_2-C_6)$alkenyl, straight or branched $(C_2-C_6)$alkynyl, $(C_3-C_{14})$aryl, $(C_3-C_{14})$-cycloalkyl, $(C_3-C_{14})$aryl$(C_1-C_6)$alkylene-, $(C_3-C_{14})$heteroaryl-$(C_1-C_6)$alkylene-, $(C_3-C_{14})$heteroaryl, $(C_3-C_{14})$heterocycloalkyl, $(C_3-C_{14})$heterocycloalkyl-$(C_1-C_6)$alkylene-, $(C_3-C_{14})$heteroaryl-$(C_3-C_6)$heterocycloalkylene-, $(C_3-C_{14})$aryl-$(C_3-C_{14})$heterocycloalkylene-, $(C_3-C_{14})$-aryl-$(C_1-C_6)$alkyl-$(C_3-C_{14})$heterocycloalkylene-, $(C_3-C_{14})$heteroaryl-$(C_1-C_6)$alkyl-$(C_3-C_{14})$heterocycloalkylene-, $(C_3-C_{14})$heterocycloalkyl-$(C_1-C_6)$alkyl-$(C_3-C_{14})$heterocycloalkylene-.

In some embodiments, $R^1$, $R^{1a}$, $R^2$, $R^{2a}$, $R^3$ and $R^{3a}$ are independently selected from the group consisting of H and straight or branched $(C_1-C_6)$alkyl, straight or branched $(C_2-C_6)$alkenyl, straight or branched $(C_2-C_6)$alkynyl, $(C_3-C_{14})$aryl, and $(C_3-C_{14})$-cycloalkyl. For instance, $R^1$, $R^{1a}$, $R^2$, $R^{2a}$, $R^3$ and $R^{3a}$ are independently selected from the group consisting of H and straight or branched $(C_1-C_6)$alkyl.

Exemplary compounds of the invention, according to some embodiments, include:

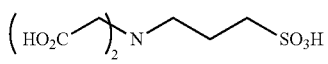

according to Formula I;

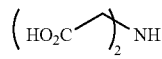

according to Formula A; and

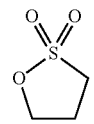

according to Formula B.

Several advantages attach to various embodiments of the invention. First, according to one embodiment, the process can be performed in an aqueous medium, such as water or substantially all water. Compounds I, A, and B are sufficiently water-soluble such that the process can be performed at high concentrations, such as 2.0-5.0 M, at 3.5 M according to one embodiment, and still produce Formula I compounds in very high yield, such as at least 85%, at least 90%, at least 95%, and at least 98%. Accordingly, in some embodiments, Formula I compounds produced according to the process can be used directly in the field without further acidification or purification.

Another advantage of the inventive process is the low pH at which the process can be performed. This is especially advantageous for acidizing operations: because Formula I compounds are charge neutral, i.e., they are not metal salts, the acidic medium is not required to, nor does it actually, liberate metal cations and, hence, the Formula I compounds maximize the sequestration or complexation of cations that are liberated in acidizing operations. The process therefore does not introduce metal cations, such as potassium or sodium, and it also does not require attenuation with additional acid, such as hydrochloric acid, in order to formulate Formula I compounds alone into a treatment blend, as is the case for commercial chelants such as KelaStim™ chelant (comprising Trilon M, BASF) and SandStim™ chelant (Halliburton). Accordingly, the process described herein yields Formula I compounds that circumvent additional preparative steps, including the purchase, transport, and handling of additional acids, that are required in the use of known chelants.

In this context, according to some embodiments, the process is performed at pH less than about 6, less than about 5, less than about 4, less than about 3, or less than about 2. An exemplary pH in one embodiment is less than about 1.

Still another advantage of the process is the relatively mild conditions under which Formula I compounds are synthesized. For instance, according to one embodiment, the reaction between Formulae A and B compounds proceeds smoothly wherein the aqueous reaction medium is substantially free of inorganic bases. That is to say, such bases are not needed to prompt reaction between Formulae A and B compounds.

In addition, according to still other embodiments, the process is advantageously performed at relatively mild temperatures, such as a temperature between about 50° C. to about 100° C., or about 60° C. to about 80° C. An exemplary reaction temperature is about 70° C.

Formula I compounds also advantageously possess three acidic functional groups with pKa of about 1 to about 6, thereby maximizing the ability of Formula I compounds to acidize and to stabilize ions. This stands in contrast to known chelants that typically feature just one functional group whose pKa is beyond the range of acidizing pH, i.e., greater than pH 7 and/or that do not have sufficient solubility below about pH 4.

The inventive process provides a ready source of Formula I compounds that also exhibit anti-corrosive and anti-scalant properties. These advantages, in addition to the metal sequestration properties described herein, are important to stimulation processes and to the preservation of oil field equipment.

Method of Treating a Subterranean Formation

One embodiment of the present invention is a method of treating a subterranean formation, comprising contacting the formation with a fluid composition comprising one or more Formula I compounds as described herein.

In some embodiments, the concentration of a Formula I compound in the composition is one in the range of about 0.1 wt % to about 80 wt %, or about 1 wt % to about 50 wt %, or about 1 wt % or more of the composition, or about 2 wt %, 3, 4, 5, 10, 15, 20, 25, 30, 40, 50, 60, 70, 80, 85, 90, 91, 92, 93, 94, 95, 96, 97, 98, 99, 99.9, or about 99.99 wt % or more.

In other embodiments, the pH of a Formula I compound fluid composition can vary. For instance, the pH is less than about 7, less than about 6, less than about 5, less than about 4, less than about 3, less than about 2, and less than about 1. In an exemplary embodiment, the pH is less than about 1. pH of the fluid composition can be adjusted by the addition of any suitable acid.

For instance, according to some embodiments, the acid is one or more mineral acids such as hydrochloric acid. Other suitable acids include but are not limited to sulfuric acid and phosphoric acid. The concentration of the acid in the fluid composition can be any suitable concentration, such as about 0.1 wt % to about 99.9 wt %, or about 1 wt % to about 99 wt %, or about 0.1 wt % or less, or about 0.5 wt %, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 44, 46, 48, 50, 55, 60, 65, 70, 75, 80, 85, 86, 87, 88, 89, 90, 91, 92, 93, 94, 95, 96, 97, 98, 99, 99.5, 99.9, or about 99.99 wt % or higher.

In other embodiments, the fluid composition comprises a carrier fluid. Any suitable proportion of the composition can be one or more downhole fluids or one or more carrier fluids. In some embodiments about 0.001 wt % to about 99.999 wt % of the composition is a downhole fluid or carrier liquid, or about 0.1 wt % to about 80 wt %, or about 1 wt % to about 50 wt %, or about 1 wt % or more of the composition, or about 2 wt %, 3, 4, 5, 10, 15, 20, 25, 30, 40, 50, 60, 70, 80, 85, 90, 91, 92, 93, 94, 95, 96, 97, 98, 99, 99.9, or about 99.99 wt % or more.

Per another embodiment, the method further includes placing the composition in a subterranean formation. The placing of the composition in the subterranean formation can include contacting the composition and any suitable part of the subterranean formation, or contacting the composition and a subterranean material, such as any suitable subterranean material. The subterranean formation can be any suitable subterranean formation. In some examples, the placing of the composition in the subterranean formation includes contacting the composition with or placing the composition in at least one of a fracture, at least a part of an area surrounding a fracture, a flow pathway, an area surrounding a flow pathway, and an area desired to be fractured. The placing of the composition in the subterranean formation can be any suitable placing and can include any suitable contacting between the subterranean formation and the composition. The placing of the composition in the subterranean formation can include at least partially depositing the composition in a fracture, flow pathway, or area surrounding the same.

In some embodiments, the method includes placing in a subterranean formation an acidizing composition comprising at least one Formula I compound as described herein. The placing of the acidizing composition in the subterranean formation can include contacting the acidizing composition and any suitable part of the subterranean formation, or contacting the acidizing composition and a subterranean material, such as any suitable subterranean material.

The subterranean formation can be any suitable subterranean formation. In some embodiments, the method is a method of acid fracturing the subterranean formation. In other embodiments, the method is a method of matrix acidizing the subterranean formation. For example, the acidizing composition can be used as or with a stimulation fluid, a clean-up fluid, a remedial treatment fluid, a pill, a diverting fluid, and an acidizing fluid. In some embodiments, method includes obtaining or providing the acidizing composition. The obtaining or providing of the acidizing composition can occur at any suitable time and at any suitable location. The obtaining or providing of the acidizing composition can occur above the surface. The obtaining or providing of the acidizing composition can occur in the subterranean formation (e.g., downhole).

In some examples, the placing of the acidizing composition in the subterranean formation (e.g., downhole) includes contacting the acidizing composition with or placing the acidizing composition in at least one of a fracture, at least a part of an area surrounding a fracture, a flow pathway, an area surrounding a flow pathway, and an area desired to be fractured. The placing of the acidizing composition in the subterranean formation can be any suitable placing and can include any suitable contacting between the subterranean formation and the acidizing composition. The placing of the acidizing composition in the subterranean formation can include at least partially depositing the acidizing composition in a fracture, flow pathway, or area surrounding the same, such as to etch or dissolve portions of the fracture face to increase permeability and corresponding production of the subterranean formation.

In still another embodiment, the method further comprises hydraulic fracturing, such as a method of hydraulic fracturing to generate a fracture or flow pathway. The placing of the composition in the subterranean formation or the contacting of the subterranean formation and the hydraulic fracturing can occur at any time with respect to one another; for example, the hydraulic fracturing occurs before, during, and/or after the contacting or placing. In some embodiments, the contacting or placing occurs during the hydraulic fracturing, such as during any suitable stage of the hydraulic fracturing, such as during at least one of a pre-pad stage (e.g., during injection of water with no proppant, and additionally optionally mid- to low-strength acid), a pad stage (e.g., during injection of fluid only with no proppant, with some viscosifier, such as to begin to break into an area and initiate fractures to produce sufficient penetration and width to allow proppant-laden later stages to enter), or a slurry stage of the fracturing (e.g., viscous fluid with proppant). The method can include performing a stimulation treatment at least one of before, during, and after placing the composition in the subterranean formation in the fracture, flow pathway, or area surrounding the same. The stimulation treatment can be, for example, at least one of perforating, acidizing, injecting of cleaning fluids, propellant stimulation, and hydraulic fracturing. In some embodiments, the stimulation treatment at least partially generates a fracture or flow pathway where the composition is placed or contacted, or the composition is placed or contacted to an area surrounding the generated fracture or flow pathway.

Other Components

In some embodiments, the composition as described herein comprises one or more surfactants. The surfactant facilitates the coating of the proppant composition on a subterranean surface causing the composition to flow into fractures and/or flow channels within the subterranean formation. The surfactant is any suitable surfactant present in any suitable proportion of the composition, such that the composition can be used as described herein. For example, about 0.000.1 wt % to about 20 wt % of the composition constitutes one or more surfactants, about 0.001 wt % to about 1 wt %, or about 0.000.1 wt % or less, or about 0.001 wt %, 0.005, 0.01, 0.02, 0.04, 0.06, 0.08, 0.1, 0.2, 0.3, 0.4, 0.5, 0.6, 0.8, 1, 2, 3, 4, 5, 6, 7, 8, 9, 10, 11, 12, 13, 14, 15, 16, 17, 18, 19, or about 20 wt % or more.

In some embodiments, the surfactant is at least one of a cationic surfactant, an anionic surfactant, and a non-ionic surfactant. In some embodiments, the ionic groups of the surfactant include counter-ions, such that the overall charge of the ionic groups is neutral, whereas in other embodiments, no counterion is present for one or more ionic groups, such that the overall charge of the one or more ionic groups is not neutral.

In some embodiments, the composition further comprises a hydrolyzable ester.

The hydrolyzable ester is any suitable hydrolyzable ester. For example, the hydrolyzable ester is a $C_1$-$C_5$ mono-, di-, tri-, or tetra-alkyl ester of a $C_2$-$C_{40}$ mono-, di-, tri-, or tetra-carboxylic acid. The hydrolyzable ester is one of dimethylglutarate, dimethyladipate, dimethylsuccinate, sorbitol, catechol, dimethylthiolate, methyl salicylate, dimethylsalicylate, and tert-butylhydroperoxide. Any suitable wt % of the composition or a cured product thereof is the hydrolyzable ester, such as about 0.01 wt % to about 20 wt %, or about 0.1 wt % to about 5 wt %, or about 0.01 wt % or less, or about 0.1 wt %, 1, 2, 3, 4, 5, 6, 8, 10, 12, 14, 16, 18, or about 20 wt % or more.

In other embodiments, the composition comprises at least one tackifier. The tackifier can be any suitable wt % of the composition or cured product thereof, such as about 0.001 wt % to about 50 wt %, about 0.01 wt % to about 30 wt %, or about 0.001 wt % or less, or about 0.01 wt %, 0.1, 1, 2, 3, 4, 5, 10, 15, 20, 25, 30, 35, 40, 45, or about 50 wt % or more. The tackifier is any suitable material having tackiness. For example, the tackifier is an adhesive or a resin. The term "resin" as used herein refers to any of numerous physically similar polymerized synthetics or chemically modified natural resins including thermoplastic materials and thermosetting materials. In some embodiments, the tackifier is at least one of a shellac, a polyamide, a silyl-modified polyamide, a polyester, a polycarbonate, a polycarbamate, a urethane, a natural resin, an epoxy-based resin, a furan-based resin, a phenolic-based resin, a urea-aldehyde resin, and a phenol/phenol formaldehyde/furfuryl alcohol resin.

In some embodiments, the tackifier is one of bisphenol A diglycidyl ether resin, butoxymethyl butyl glycidyl ether resin, bisphenol A-epichlorohydrin resin, and bisphenol F resin. In other embodiments, the tackifier is one of an acrylic acid polymer, an acrylic acid ester polymer, an acrylic acid homopolymer, an acrylic acid ester homopolymer, poly (methyl acrylate), poly(butyl acrylate), poly(2-ethylhexyl acrylate), an acrylic acid ester copolymer, a methacrylic acid derivative polymer, a methacrylic acid homopolymer, a methacrylic acid ester homopolymer, poly(methyl methacrylate), poly(butyl methacrylate), poly(2-ethylhexyl methacrylate), an acrylamidomethylpropane sulfonate polymer or copolymer or derivative thereof, and an acrylic acid/acrylamidomethylpropane sulfonate copolymer. In still other embodiments, the tackifier is a trimer acid, a fatty acid, a fatty acid-derivative, maleic anhydride, acrylic acid, a polyester, a polycarbonate, a polycarbamate, an aldehyde, formaldehyde, a dialdehyde, glutaraldehyde, a hemiacetal, an aldehyde-releasing compound, a diacid halide, a dihalide, a dichloride, a dibromide, a polyacid anhydride, citric acid, an epoxide, furfuraldehyde, an aldehyde condensate, a silyl-modified polyamide, and a condensation reaction product of a polyacid and a polyamine.

In some embodiments, the tackifier includes an amine-containing polymer and/or is hydrophobically-modified. In some embodiments, the tackifier includes one of a polyamine (e.g., spermidine and spermine), a polyimine (e.g., poly(ethylene imine) and poly(propylene imine)), a polyamide, poly(2-(N,N-dimethylamino)ethyl methacrylate), poly(2-(N,N-diethylamino)ethyl methacrylate), poly (vinyl imidazole), and a copolymer including monomers of at least one of the foregoing and monomers of at least one non-amine-containing polymer such as of at least one of polyethylene, polypropylene, polyethylene oxide, polypropylene oxide, polyvinylpyridine, polyacrylic acid, polyacrylate, and polymethacrylate. The hydrophobic modification is any suitable hydrophobic modification, such as at least one $C_4$-$C_{30}$ hydrocarbyl including at least one of a straight chain, a branched chain, an unsaturated C—C bond, an aryl group, and any combination thereof.

In some embodiments where viscosity is modified, the composition includes one or more viscosifiers. The viscosifier is any suitable viscosifier. The viscosifier provides an increased viscosity of the composition before injection into the subterranean formation, at the time of injection into the subterranean formation, during travel through a tubular disposed in a borehole, once the composition reaches a particular subterranean location, or some period of time after the composition reaches a particular subterranean location. In some embodiments, the viscosifier can be about 0.000.1 wt % to about 10 wt % of the composition or a cured product thereof, about 0.004 wt % to about 0.01 wt %, or about 0.000.1 wt % or less, 0.000.5 wt %, 0.001, 0.005, 0.01, 0.05, 0.1, 0.5, 1, 2, 3, 4, 5, 6, 7, 8, 9, or about 10 wt % or more.

The viscosifier includes at least one of a substituted or unsubstituted polysaccharide, and a substituted or unsubstituted polyalkene (e.g., a polyethylene, wherein the ethylene unit is substituted or unsubstituted, derived from the corresponding substituted or unsubstituted ethene), wherein the polysaccharide or polyalkene is crosslinked or uncrosslinked. Exemplary viscosifiers include a polymer including at least one monomer selected from the group consisting of ethylene glycol, acrylamide, vinyl acetate, 2-acrylamidomethylpropane sulfonic acid or its salts, trimethylammoniumethyl acrylate halide, and trimethylammoniumethyl methacrylate halide. The viscosifier can include a crosslinked gel or a crosslinkable gel. The viscosifier can include at least one of a linear polysaccharide, and a poly(($C_2$-$C_{10}$)alkene), wherein the ($C_2$-$C_{10}$)alkene is substituted or unsubstituted. The viscosifier can include at least one of poly(acrylic acid) or ($C_1$-$C_5$)alkyl esters thereof, poly(methacrylic acid) or ($C_1$-$C_5$)alkyl esters thereof, poly(vinyl acetate), poly(vinyl alcohol), poly(ethylene glycol), poly(vinyl pyrrolidone), polyacrylamide, poly (hydroxyethyl methacrylate), alginate, chitosan, curdlan, dextran, emulsan, a galactoglucopolysaccharide, gellan, glucuronan, N-acetyl-glucosamine, N-acetyl-heparosan, hyaluronic acid, kefiran, lentinan, levan, mauran, pullulan, scleroglucan, schizophyllan, stewartan, succinoglycan, xanthan, welan, derivatized starch, tamarind, tragacanth, guar gum, derivatized guar (e.g., hydroxypropyl guar, carboxy methyl guar, or carboxymethyl hydroxypropyl guar), gum ghatti, gum arabic, locust bean gum, and derivatized cellulose (e.g., carboxymethyl cellulose, hydroxyethyl cellulose, carboxymethyl hydroxyethyl cellulose, hydroxypropyl cellulose, or methyl hydroxy ethyl cellulose).

In some embodiments, the viscosifier is at least one of a poly(vinyl alcohol) homopolymer, poly(vinyl alcohol) copolymer, a crosslinked poly(vinyl alcohol) homopolymer, and a crosslinked poly(vinyl alcohol) copolymer. The viscosifier can include a poly(vinyl alcohol) copolymer or a crosslinked poly(vinyl alcohol) copolymer including at least one of a graft, linear, branched, block, and random copolymer of vinyl alcohol and at least one of a substituted or unsubstituted $(C_2-C_{50})$hydrocarbyl having at least one aliphatic unsaturated C—C bond therein, and a substituted or unsubstituted $(C_2-C_{50})$alkene. The viscosifier can include a poly (vinyl alcohol) copolymer or a crosslinked poly(vinyl alcohol) copolymer including at least one of a graft, linear, branched, block, and random copolymer of vinyl alcohol and at least one of vinyl phosphonic acid, vinylidene diphosphonic acid, substituted or unsubstituted 2-acrylamido-2-methylpropanesulfonic acid, a substituted or unsubstituted $(C_1-C_{20})$alkenoic acid, propenoic acid, butenoic acid, pentenoic acid, hexenoic acid, octenoic acid, nonenoic acid, decenoic acid, acrylic acid, methacrylic acid, hydroxypropyl acrylic acid, acrylamide, fumaric acid, methacrylic acid, hydroxypropyl acrylic acid, vinyl phosphonic acid, vinylidene diphosphonic acid, itaconic acid, crotonic acid, mesoconic acid, citraconic acid, styrene sulfonic acid, allyl sulfonic acid, methallyl sulfonic acid, vinyl sulfonic acid, and a substituted or unsubstituted $(C_1-C_{20})$alkyl ester thereof. The viscosifier can include a poly(vinyl alcohol) copolymer or a crosslinked poly(vinyl alcohol) copolymer including at least one of a graft, linear, branched, block, and random copolymer of vinyl alcohol and at least one of vinyl acetate, vinyl propanoate, vinyl butanoate, vinyl pentanoate, vinyl hexanoate, vinyl 2-methyl butanoate, vinyl 3-ethyl-pentanoate, and vinyl 3-ethylhexanoate, maleic anhydride, a substituted or unsubstituted $(C_1-C_{20})$alkenoic substituted or unsubstituted $(C_1-C_{20})$alkanoic anhydride, a substituted or unsubstituted $(C_1-C_{20})$alkenoic substituted or unsubstituted $(C_1-C_{20})$alkenoic anhydride, propenoic acid anhydride, butenoic acid anhydride, pentenoic acid anhydride, hexenoic acid anhydride, octenoic acid anhydride, nonenoic acid anhydride, decenoic acid anhydride, acrylic acid anhydride, fumaric acid anhydride, methacrylic acid anhydride, hydroxypropyl acrylic acid anhydride, vinyl phosphonic acid anhydride, vinylidene diphosphonic acid anhydride, itaconic acid anhydride, crotonic acid anhydride, mesoconic acid anhydride, citraconic acid anhydride, styrene sulfonic acid anhydride, allyl sulfonic acid anhydride, methallyl sulfonic acid anhydride, vinyl sulfonic acid anhydride, and an N—$(C_1-C_{10})$alkenyl nitrogen containing substituted or unsubstituted $(C_1-C_{10})$heterocycle. The viscosifier can include a poly(vinyl alcohol) copolymer or a crosslinked poly(vinyl alcohol) copolymer including at least one of a graft, linear, branched, block, and random copolymer that includes a poly(vinylalcohol/acrylamide) copolymer, a poly (vinylalcohol/2-acrylamido-2-methylpropanesulfonic acid) copolymer, a poly (acrylamide/2-acrylamido-2-methylpropanesulfonic acid) copolymer, or a poly(vinylalcohol/N-vinylpyrrolidone) copolymer. The viscosifier can include a crosslinked poly(vinyl alcohol) homopolymer or copolymer including a crosslinker including at least one of chromium, aluminum, antimony, zirconium, titanium, calcium, boron, iron, silicon, copper, zinc, magnesium, and an ion thereof. The viscosifier can include a crosslinked poly(vinyl alcohol) homopolymer or copolymer including a crosslinker including at least one of an aldehyde, an aldehyde-forming compound, a carboxylic acid or an ester thereof, a sulfonic acid or an ester thereof, a phosphonic acid or an ester thereof, an acid anhydride, and an epihalohydrin.

In some embodiments, the composition comprises one or more breakers. The breaker is any suitable breaker, such that the surrounding fluid (e.g., a fracturing fluid) is at least partially broken for more complete and more efficient recovery thereof, such as at the conclusion of the hydraulic fracturing treatment. In some embodiments, the breaker is encapsulated or otherwise formulated to give a delayed-release or a time-release breaker, such that the surrounding liquid remains viscous for a suitable amount of time prior to breaking. The breaker is any suitable breaker; such as a compound that includes a $Na^+$, $K^+$, $Li^+$, $Zn^+$, $NH_4^+$, $Fe^{2+}$, $Fe^{3+}$, $Cu^{1+}$, $Cu^{2+}$, $Ca^{2+}$, $Mg^{2+}$, $Zn^{2+}$, and an $Al^{3+}$ salt of a chloride, fluoride, bromide, phosphate, or sulfate ion. In some examples, the breaker can be an oxidative breaker or an enzymatic breaker. An oxidative breaker is at least one of a $Na^+$, $K^+$, $Li^+$, $Zn^+$, $NH_4^+$, $Fe^{2+}$, $Fe^{3+}$, $Cu^{1+}$, $Cu^{2+}$, $Ca^{2+}$, $Mg^{2+}$, $Zn^{2+}$, and an $Al^{3+}$ salt of a persulfate, percarbonate, perborate, peroxide, perphosphate, permanganate, chlorite, or hyperchlorite ion. An enzymatic breaker is at least one of an alpha or beta amylase, amyloglucosidase, oligoglucosidase, invertase, maltase, cellulase, hemi-cellulase, and mannanohydrolase. The breaker can be about 0.001 wt % to about 30 wt % of the composition, or about 0.01 wt % to about 5 wt %, or about 0.001 wt % or less, or about 0.005 wt %, 0.01, 0.05, 0.1, 0.5, 1, 2, 3, 4, 5, 6, 8, 10, 12, 14, 16, 18, 20, 22, 24, 26, 28, or about 30 wt % or more.

In accordance with one embodiment, the composition comprises any suitable fluid in addition to those otherwise described herein. For example, the fluid is at least one of crude oil, dipropylene glycol methyl ether, dipropylene glycol dimethyl ether, dipropylene glycol methyl ether, dipropylene glycol dimethyl ether, dimethyl formamide, diethylene glycol methyl ether, ethylene glycol butyl ether, diethylene glycol butyl ether, butylglycidyl ether, propylene carbonate, D-limonene, a $C_2-C_{40}$ fatty acid $C_1-C_{10}$ alkyl ester (e.g., a fatty acid methyl ester), tetrahydrofurfuryl methacrylate, tetrahydrofurfuryl acrylate, 2-butoxy ethanol, butyl acetate, butyl lactate, furfuryl acetate, dimethyl sulfoxide, dimethyl formamide, a petroleum distillation product of fraction (e.g., diesel, kerosene, napthas, and the like) mineral oil, a hydrocarbon oil, a hydrocarbon including an aromatic carbon-carbon bond (e.g., benzene, toluene), a hydrocarbon including an alpha olefin, xylenes, an ionic liquid, methyl ethyl ketone, an ester of oxalic, maleic or succinic acid, methanol, ethanol, propanol (iso- or normal-), butyl alcohol (iso-, tert-, or normal-), an aliphatic hydrocarbon (e.g., cyclohexanone, hexane), water, brine, produced water, flowback water, brackish water, and sea water. The fluid constitutes about 0.001 wt % to about 99.999 wt % of the composition or about 0.001 wt % or less, 0.01 wt %, 0.1, 1, 2, 3, 4, 5, 6, 8, 10, 15, 20, 25, 30, 35, 40, 45, 50, 55, 60, 65, 70, 75, 80, 85, 90, 95, 96, 97, 98, 99, 99.9, 99.99, or about 99.999 wt % or more.

In other embodiments, the composition comprises a downhole fluid. The composition can be combined with any suitable downhole fluid before, during, or after the placement of the composition in the subterranean formation or the contacting of the composition and the subterranean material. In some examples, the composition is combined with a downhole fluid above the surface, and then the combined composition is placed in a subterranean formation or contacted with a subterranean material. In another example, the composition is injected into a subterranean formation to combine with a downhole fluid, and the combined composition is contacted with a subterranean material or is considered to be placed in the subterranean formation.

In some embodiments, the downhole fluid is an aqueous or oil-based fluid including a fracturing fluid, spotting fluid, clean-up fluid, completion fluid, remedial treatment fluid, abandonment fluid, pill, cementing fluid, packer fluid, or a combination thereof. The placement of the composition in the subterranean formation can include contacting the subterranean material and the mixture. The downhole fluid constitutes any suitable weight percent of the composition, such as about 0.001 wt % to about 99.999 wt %, about 0.01 wt % to about 99.99 wt %, about 0.1 wt % to about 99.9 wt %, about 20 wt % to about 90 wt %, or about 0.001 wt % or less, or about 0.01 wt %, 0.1, 1, 2, 3, 4, 5, 10, 15, 20, 30, 40, 50, 60, 70, 80, 85, 90, 91, 92, 93, 94, 95, 96, 97, 98, 99, 99.9, 99.99 wt %, or about 99.999 wt %.

In some embodiments, the composition includes an amount of any suitable material used in a downhole fluid. For example, the composition includes water, saline, aqueous base, acid, oil, organic solvent, synthetic fluid oil phase, aqueous solution, alcohol or polyol, cellulose, starch, alkalinity control agents, acidity control agents, density control agents, density modifiers, emulsifiers, dispersants, polymeric stabilizers, crosslinking agents, polyacrylamide, a polymer or combination of polymers, antioxidants, heat stabilizers, foam control agents, solvents, diluents, plasticizer, filler or inorganic particle, pigment, dye, precipitating agent, rheology modifier, oil-wetting agents, set retarding additives, surfactants, gases, weight reducing additives, heavy-weight additives, lost circulation materials, filtration control additives, salts, fibers, thixotropic additives, breakers, crosslinkers, rheology modifiers, curing accelerators, curing retarders, pH modifiers, chelating agents, scale inhibitors, enzymes, resins, water control materials, oxidizers, markers, or a combination thereof.

System

In accordance with an embodiment, the invention provides a system that uses or that can be generated by use of an embodiment of the composition described herein in a subterranean formation, or that can perform or be generated by performance of a method for using the composition described herein. For instance, the system includes a composition and a subterranean formation including the composition therein. In some embodiments, the composition in the system includes a downhole fluid, or the system comprises a mixture of the composition and downhole fluid. In other embodiments, the system comprises a tubular and a pump configured to pump the composition into the subterranean formation through the tubular.

Some embodiments provide a system configured for delivering the composition described herein to a subterranean location and for using the composition therein, such as for a fracturing operation (e.g., pre-pad, pad, slurry, or finishing stages). In some embodiments, the system or apparatus includes a pump fluidly coupled to a tubular (e.g., any suitable type of oilfield pipe, such as pipeline, drill pipe, production tubing, and the like), the tubular containing a composition as described herein.

In some embodiments, the system comprises a drillstring disposed in a wellbore, the drillstring including a drill bit at a downhole end of the drillstring. The system can also include an annulus between the drillstring and the wellbore. Further, in accordance with one embodiment, the system includes a pump configured to circulate the composition through the drill string, through the drill bit, and back above-surface through the annulus. In some embodiments, the system includes a fluid processing unit configured to process the composition exiting the annulus to generate a cleaned drilling fluid for recirculation through the wellbore.

The pump is a high pressure pump in some embodiments. As used herein, the term "high pressure pump" refers to a pump that is capable of delivering a fluid to a subterranean formation (e.g., downhole) at a pressure of about 1000 psi or greater. A high pressure pump can be used when it is desired to introduce the composition to a subterranean formation at or above a fracture gradient of the subterranean formation, but it can also be used in cases where fracturing is not desired. In some embodiments, the high pressure pump can be capable of fluidly conveying particulate matter, such as proppant particulates, into the subterranean formation. Suitable high pressure pumps are known to one having ordinary skill in the art and can include floating piston pumps and positive displacement pumps.

In other embodiments, the pump is a low pressure pump. As used herein, the term "low pressure pump" refers to a pump that operates at a pressure of about 1000 psi or less. In some embodiments, a low pressure pump can be fluidly coupled to a high pressure pump that is fluidly coupled to the tubular. That is, in such embodiments, the low pressure pump is configured to convey the composition to the high pressure pump. In such embodiments, the low pressure pump can "step up" the pressure of the composition before it reaches the high pressure pump.

In some embodiments, the system described herein further includes a mixing tank that is upstream of the pump and in which the composition is formulated. In various embodiments, the pump (e.g., a low pressure pump, a high pressure pump, or a combination thereof) conveys the composition from the mixing tank or other source of the composition to the tubular. In other embodiments, however, the composition e formulated offsite and transported to a worksite, in which case the composition is introduced to the tubular via the pump directly from its shipping container (e.g., a truck, a railcar, a barge, or the like) or from a transport pipeline. In either case, the composition is drawn into the pump, elevated to an appropriate pressure, and then introduced into the tubular for delivery to the subterranean formation.

With reference to FIG. 1, the composition directly or indirectly affects one or more components or pieces of equipment associated with a wellbore drilling assembly 100, according to one or more embodiments. While FIG. 1 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 100 can include a drilling platform 102 that supports a derrick 104 having a traveling block 106 for raising and lowering a drill string 108. The drill string 108 may include, but is not limited to, drill pipe and coiled tubing, as generally known to those skilled in the art. A kelly 110 supports the drill string 108 as it is lowered through a rotary table 112. A drill bit 114 is attached to the distal end of the drill string 108 and is driven either by a downhole motor and/or via rotation of the drill string 108 from the well surface. As the bit 114 rotates, it creates a wellbore 116 that penetrates various subterranean formations 118.

A pump 120 (e.g., a mud pump) circulates drilling fluid 122 through a feed pipe 124 and to the kelly 110, which conveys the drilling fluid 122 downhole through the interior of the drill string 108 and through one or more orifices in the drill bit 114. The drilling fluid 122 is then circulated back to the surface via an annulus 126 defined between the drill string 108 and the walls of the wellbore 116. At the surface, the recirculated or spent drilling fluid 122 exits the annulus 126 and may be conveyed to one or more fluid processing unit(s) 128 via an interconnecting flow line 130. After passing through the fluid processing unit(s) 128, a "cleaned" drilling fluid 122 is deposited into a nearby retention pit 132 (e.g., a mud pit). While illustrated as being arranged at the outlet of the wellbore 116 via the annulus 126, those skilled in the art will readily appreciate that the fluid processing unit(s) 128 may be arranged at any other location in the drilling assembly 100 to facilitate its proper function, without departing from the scope of the disclosure.

The composition may be added to, among other things, a drilling fluid 122 via a mixing hopper 134 communicably coupled to or otherwise in fluid communication with the retention pit 132. The mixing hopper 134 may include, but is not limited to, mixers and related mixing equipment known to those skilled in the art. In other embodiments, however, the composition is added to, among other things, a drilling fluid 122 at any other location in the drilling assembly 100. In at least one embodiment, for example, there is more than one retention pit 132, such as multiple retention pits 132 in series. Moreover, the retention pit 132 can represent one or more fluid storage facilities and/or units where the composition may be stored, reconditioned, and/or regulated until added to a drilling fluid 122.

As mentioned above, the composition may directly or indirectly affect the components and equipment of the drilling assembly 100. For example, the composition may directly or indirectly affect the fluid processing unit(s) 128, which may include, but is not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, or any fluid reclamation equipment. The fluid processing unit(s) 128 may further include one or more sensors, gauges, pumps, compressors, and the like used to store, monitor, regulate, and/or recondition the composition.

The composition may directly or indirectly affect the pump 120, which is intended to represent one or more of any conduits, pipelines, trucks, tubulars, and/or pipes used to fluidically convey the composition downhole, any pumps, compressors, or motors (e.g., topside or downhole) used to drive the composition into motion, any valves or related joints used to regulate the pressure or flow rate of the composition, and any sensors (e.g., pressure, temperature, flow rate, and the like), gauges, and/or combinations thereof, and the like. The composition may also directly or indirectly affect the mixing hopper 134 and the retention pit 132 and their assorted variations.

The composition can also directly or indirectly affect various downhole equipment and tools that comes into contact with the composition such as, but not limited to, the drill string 108, any floats, drill collars, mud motors, downhole motors, and/or pumps associated with the drill string 108, and any measurement while drilling (MWD)/logging while drilling (LWD) tools and related telemetry equipment, sensors, or distributed sensors associated with the drill string 108. The composition may also directly or indirectly affect any downhole heat exchangers, valves and corresponding actuation devices, tool seals, packers and other wellbore isolation devices or components, and the like associated with the wellbore 116.

While not specifically illustrated herein, the composition may also directly or indirectly affect any transport or delivery equipment used to convey the composition to the drilling assembly 100 such as, for example, any transport vessels, conduits, pipelines, trucks, tubulars, and/or pipes used to fluidically move the composition from one location to another, any pumps, compressors, or motors used to drive the composition into motion, any valves or related joints used to regulate the pressure or flow rate of the composition, and any sensors (e.g., pressure and temperature), gauges, and/or combinations thereof, and the like.

Figure 2:
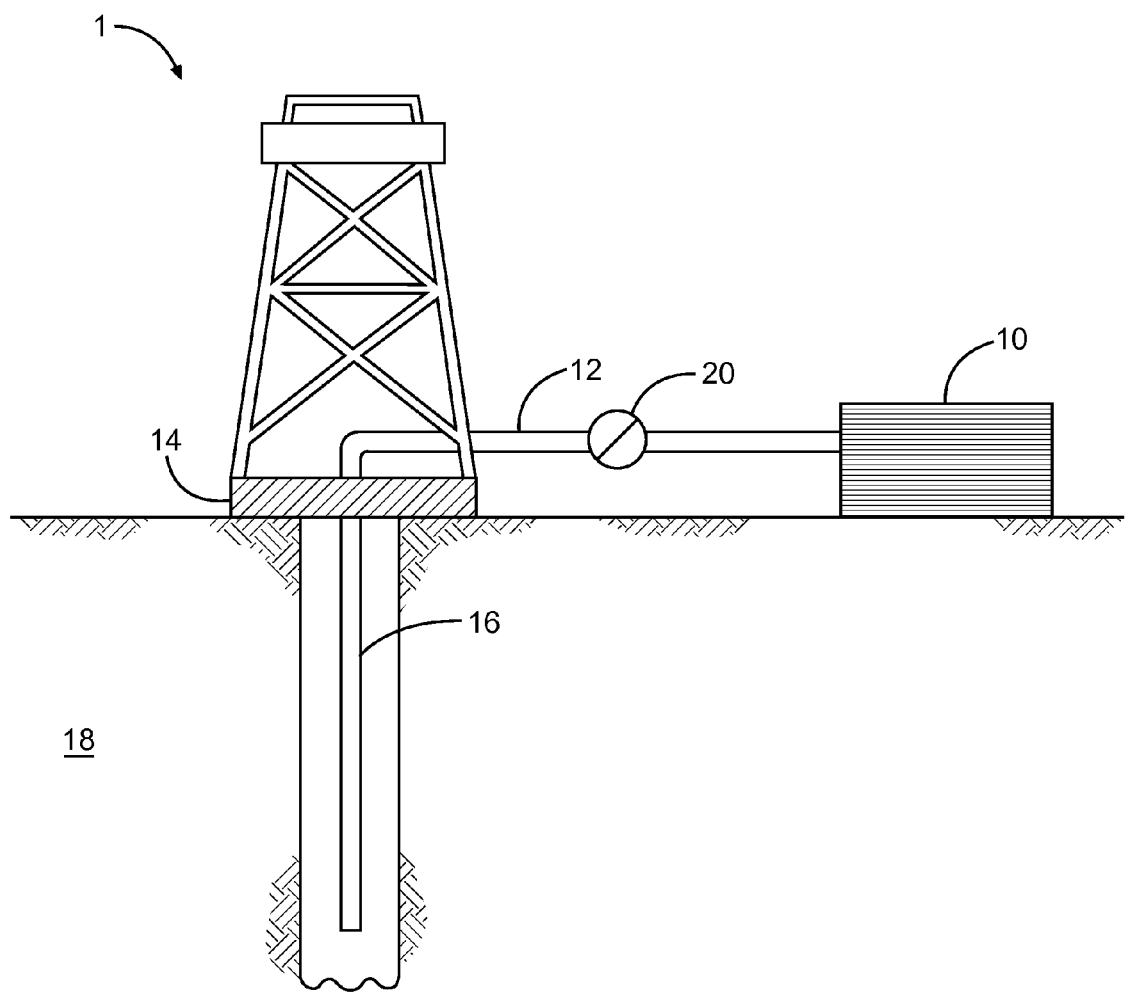
FIG. 2 illustrates a system for delivering a composition to a subterranean formation in accordance with various embodiments.
Figure 3:
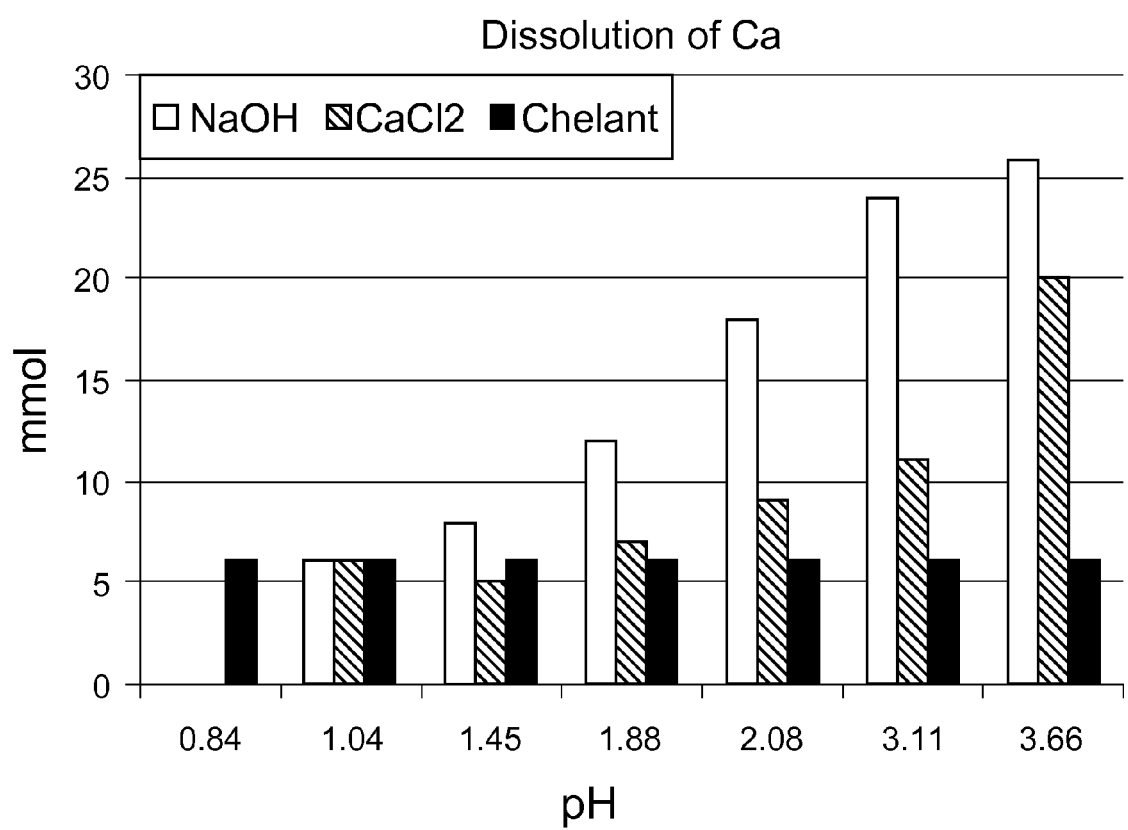
FIG. 3 illustrates the efficacy of a Formula I compound as described herein for dissolving $Ca^{2+}$ in aqueous solution.

FIG. 2 shows an illustrative schematic of systems that can deliver embodiments of the compositions of the present invention to a subterranean location, according to one or more embodiments. It should be noted that while FIG. 2 generally depicts a land-based system or apparatus, like systems and apparatuses can be operated in subsea locations as well.

Embodiments of the present invention can have a different scale than that depicted in FIG. 2. As depicted in FIG. 2, system or apparatus 1 can include mixing tank 10, in which an embodiment of the composition can be formulated. The composition can be conveyed via line 12 to wellhead 14, where the composition enters tubular 16, with tubular 16 extending from wellhead 14 into subterranean formation 18. Upon being ejected from tubular 16, the composition can subsequently penetrate into subterranean formation 18. Pump 20 can be configured to raise the pressure of the composition to a desired degree before its introduction into tubular 16. It is to be recognized that system or apparatus 1 is merely exemplary in nature and various additional components can be present that have not necessarily been depicted in FIG. 2 in the interest of clarity. In some examples, additional components that can be present include supply hoppers, valves, condensers, adapters, joints, gauges, sensors, compressors, pressure controllers, pressure sensors, flow rate controllers, flow rate sensors, temperature sensors, and the like.

Although not depicted in FIG. 2, at least part of the composition can, in some embodiments, flow back to wellhead 14 and exit subterranean formation 18. The composition that flows back can be substantially diminished in the concentration of various components therein. In some embodiments, the composition that has flowed back to wellhead 14 can subsequently be recovered, and in some examples reformulated, and recirculated to subterranean formation 18.

The composition of the invention can also directly or indirectly affect the various downhole or subterranean equipment and tools that can come into contact with the composition during operation. Such equipment and tools can include wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, and the like), logging tools and related telemetry equipment, actuators (e.g., electromechanical devices, hydromechanical devices, and the like), sliding sleeves, production sleeves, plugs, screens, filters, flow control devices (e.g., inflow control devices, autonomous inflow control devices, outflow control devices, and the like), couplings (e.g., electro-hy-

EXAMPLES

Various embodiments of the present invention can be better understood by reference to the following Examples that are offered by way of illustration. The present invention is not limited to the Examples given herein.

Example 1

Synthesis of 2,2'-((3-sulfopropyl)azanediyl)diacetic acid

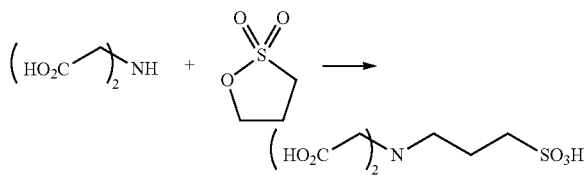

2,2'-azanediyldiacetic acid 15.5 g, 116 mol) and 1,2-oxathiolane-2,2-dioxide 14.2 g, 116 mol) were combined in 35 mL water. The mixture was stirred at 85° C. for 4 h. Reaction monitored by NMR and completion was verified by disappearance of NMR resonances of starting material. The resulting aqueous solution contained 2,2'-((3-sulfopropyl)azanediyl)diacetic acid in essentially quantitative yield as determined by NMR. The solution was used without purification or further manipulation.

Example 2

Dissolution of Calcium (II)

The purpose of this example is to demonstrate the stabilization of calcium (II) ion by a Formula I compound.

An aliquot of the chelant solution prepared in Example 1 was diluted to 0.6 M at a total volume of 10 mL, brought to pH 1, then charged into a vessel. Six quantities of $CaCl_2$ and NaOH were sequentially added to the chelant solution, resulting in the final concentrations shown in the table below, in order to determine the pH where formation of CaOH would ensue.

TABLE 1

| NaOH (mmol) | $CaCl_2$ (mmol) | $Ca^{2+}$ (g) Total | $Ca(OH)_2$ (g)/10 mL | * $Ca(OH)_2$ g/100 mL |
|---|---|---|---|---|
| 0 | 0 | 0 | 0 | 0 |
| 6 | 4 | 0.16 | 0.3 | 3 |
| 8 | 5 | 0.2 | 0.375 | 3.75 |
| 12 | 7 | 0.28 | 0.525 | 5.25 |
| 18 | 9 | 0.36 | 0.675 | 6.75 |
| 24 | 11 | 0.44 | 0.825 | 8.25 |
| 25.8 | 20 | 0.8 | 1.5 | 15 |

* $Ca(OH)_2$ Ksp = 0.173(g)/100 mL (20° C.) or 0.0173(g)/10 mL

FIG. 1 graphs the results, showing that calcium ion is stabilized by the chelant up to pH 3.6. Specifically, an increase in pH favors the formation of $Ca(OH)_2$, based upon the number of mmol of both $CaCl_2$ and NaOH added. Reported solubility of $Ca(OH)_2$ in water ranges from 0.066 g/100 mL to 0.189 g/100 mL, where solubility increases as temperature decreases. Hence, the amounts of $Ca(OH)_2$ depicted in the Table 1 suggest nearly 10 times the concentration of $Ca(OH)_2$ dissolved in aqueous solutions containing the product Example 1 as compared to pure water.

For instance, dissolution of 11 mmol of $CaCl_2$ (limiting reagent) and 24 mmol of NaOH in 10 mL of water suggests the potential formation of 0.814 g of $Ca(OH)_2$. This amount is over 10 times the amount of $Ca(OH)_2$ that could be solubilized based on known solubility of $Ca(OH)_2$ (0.169 g/100 mL). In addition, control studies show that $Ca(OH)_2$ "Ca" remains in solution in larger quantities and for extended periods of time when employing the material synthesized in example 1.

Example 3

Dissolution of Calcium Fluoride

The purpose of this example is to demonstrate the ability of a Formula I compound to solubilize aqueous calcium fluoride.

A control solution was prepared by dissolving $CaCl_2$ (0.6 M) and ammonium bifluoride ($NH_4HF_2$, 0.6 M) in 5 mL water. A test solution identical in all respects to the control solution also was prepared with the addition of 0.6 M of the chelant (pH 1) prepared as in Example 1.

To the control solution was added $NH_4OH$ in an amount sufficient to raise pH to 7. A separate quantity of $NH_4OH$ was added to the chelant solution to raise pH of the chelant solution to about 4.

Within about 5 minutes, $CaF_2$ precipitated from and settled to the bottom of the control solution. In contrast, the chelant solution exhibited some precipitation of $CaF_2$, but even after 24 h, no $CaF_2$ had settled but instead remained in suspension. The results demonstrate that the chelant according to Formula I is an effective stabilizer of $CaF_2$.

We claim:

1. A method of treating a subterranean formation, the method comprising placing into the subterranean formation a composition comprising a compound according to Formula I:

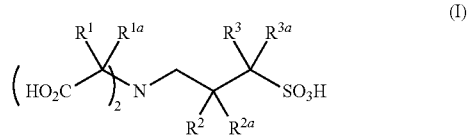

that is prepared by a process comprising contacting a compound of Formula A:

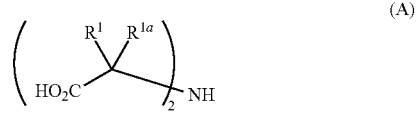

with a compound of Formula B:

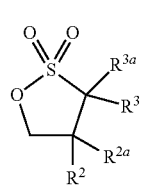

wherein
R$^1$, R$^{1a}$, R$^2$, R$^{2a}$, R$^3$ and R$^{3a}$ are independently selected from the group consisting of H, —OH, halo, straight or branched (C$_1$-C$_6$)alkyl, straight or branched (C$_2$-C$_6$)alkenyl, straight or branched (C$_2$-C$_6$)alkynyl, (C$_3$-C$_{14}$)aryl, (C$_3$-C$_{14}$)-cycloalkyl, (C$_3$-C$_{14}$)aryl(C$_1$-C$_6$)alkylene-, (C$_3$-C$_{14}$)heteroaryl-(C$_1$-C$_6$)alkylene-, (C$_3$-C$_{14}$)heteroaryl, (C$_3$-C$_{14}$)heterocycloalkyl, (C$_3$-C$_{14}$)heterocycloalkyl-(C$_1$-C$_6$)alkylene-, (C$_3$-C$_{14}$)heteroaryl-(C$_3$-C$_6$)heterocycloalkylene-, (C$_3$-C$_{14}$)aryl-(C$_3$-C$_{14}$)heterocycloalkylene-, (C$_3$-C$_{14}$)-aryl-(C$_1$-C$_6$)alkyl-(C$_3$-C$_{14}$)heterocycloalkylene-, (C$_3$-C$_{14}$)heteroaryl-(C$_1$-C$_6$)alkyl-(C$_3$-C$_{14}$)heterocycloalkylene-, (C$_3$-C$_{14}$)heterocycloalkyl-(C$_1$-C$_6$)alkyl-(C$_3$-C$_{14}$)heterocycloalkylene-.

2. The method according to claim 1, wherein the placing comprises placing the composition in at least one of a fracture and flow path in the subterranean formation.

3. The method according to claim 2, wherein the fracture is present in the subterranean formation at the time when the composition is placed into the subterranean formation.

4. The method according to claim 2, wherein the method further comprises forming the fracture or flow path.

5. The method according to claim 1, wherein the placing comprises gravel packing.

6. The method according to claim 1, further comprising fracturing the subterranean formation to form at least one fracture in the subterranean formation.

7. The method according to claim 1, wherein the composition further comprises a carrier fluid.

8. The method according to claim 1, further comprising combining the composition with an aqueous or oil-based fluid comprising a fracturing fluid, spotting fluid, clean-up fluid, completion fluid, remedial treatment fluid, abandonment fluid, pill, packer fluid, or a combination thereof.

9. A system for performing the method of claim 1, the system comprising:
a tubular disposed in the subterranean formation; and
a pump configured to pump the composition in the subterranean formation through the tubular.

10. A process for synthesizing a compound according to Formula I:

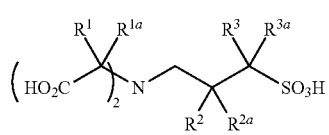

(I)

comprising contacting a compound of Formula A:

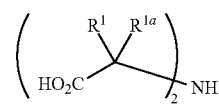

(A)

with a compound of Formula B:

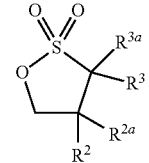

(B)

wherein
R$^1$, R$^{1a}$, R$^2$, R$^{2a}$, R$^3$ and R$^{3a}$ are independently selected from the group consisting of H, —OH, halo, straight or branched (C$_1$-C$_6$)alkyl, straight or branched (C$_2$-C$_6$)alkenyl, straight or branched (C$_2$-C$_6$)alkynyl, (C$_3$-C$_{14}$)aryl, (C$_3$-C$_{14}$)-cycloalkyl, (C$_3$-C$_{14}$)aryl(C$_1$-C$_6$)alkylene-, (C$_3$-C$_{14}$)heteroaryl-(C$_1$-C$_6$)alkylene-, (C$_3$-C$_{14}$)heteroaryl, (C$_3$-C$_{14}$)heterocycloalkyl, (C$_3$-C$_{14}$)heterocycloalkyl-(C$_1$-C$_6$)alkylene-, (C$_3$-C$_{14}$)heteroaryl-(C$_3$-C$_6$)heterocycloalkylene-, (C$_3$-C$_{14}$)aryl-(C$_3$-C$_{14}$)heterocycloalkylene-, (C$_3$-C$_{14}$)-aryl-(C$_1$-C$_6$)alkyl-(C$_3$-C$_{14}$)heterocycloalkylene-, (C$_3$-C$_{14}$)heteroaryl-(C$_1$-C$_6$)alkyl-(C$_3$-C$_{14}$)heterocycloalkylene-, (C$_3$-C$_{14}$)heterocycloalkyl-(C$_1$-C$_6$)alkyl-(C$_3$-C$_{14}$)heterocycloalkylene-.

11. The process according to claim 10, wherein R$^1$, R$^{1a}$, R$^2$, R$^{2a}$, R$^3$ and R$^{3a}$ are independently selected from the group consisting of H and straight or branched (C$_1$-C$_6$)alkyl, straight or branched (C$_2$-C$_6$)alkenyl, straight or branched (C$_2$-C$_6$)alkynyl, (C$_3$-C$_{14}$)aryl, and (C$_3$-C$_{14}$)-cycloalkyl.

12. The process according to claim 11, wherein R$^1$, R$^{1a}$, R$^2$, R$^{2a}$, R$^3$ and R$^{3a}$ are independently selected from the group consisting of H and straight or branched (C$_1$-C$_6$)alkyl.

13. The process according to claim 12, wherein the compound according to Formula I is:

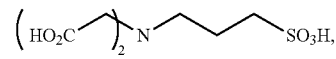

the compound according to Formula A is

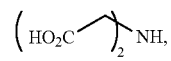

and
the compound according to Formula B is:

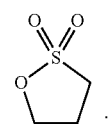

14. The process according to claim 10, wherein the contacting is performed in an aqueous medium.

15. The process according to claim 14, wherein the pH of the aqueous medium is less than about 6.

16. The process according to claim 15, wherein the pH of the aqueous medium is less than about 3.

17. The process according to claim 16, wherein the pH of the aqueous medium is less than about 2.

18. The process according to claim 17, wherein the pH of the aqueous medium is less than about 1.

19. The process according to claim 14, wherein the aqueous medium is substantially free of inorganic bases.

20. The process according to claim 10, wherein the contacting occurs at a temperature between about 50° C. and about 100° C.

21. The process according to claim 20, wherein the temperature is between about 60° C. and about 80° C.

22. The process according to claim 21, wherein the temperature is about 70° C.

* * * * *